United States Patent [19]

Kischka et al.

[11] Patent Number: 5,500,218
[45] Date of Patent: Mar. 19, 1996

[54] METHOD OF PREVENTING COLORING OF SKIN ADJACENT THE HAIRLINE DURING DYEING OF HAIR

[75] Inventors: Karl-Heinz Kischka, Darmstadt, Germany; Toshimasa Furukawa, Chiba; Akiyo Maezawa, Tokyo, both of Japan

[73] Assignee: Wella Aktiengesellschaft, Darmstadt, Germany

[21] Appl. No.: 137,109

[22] PCT Filed: Jan. 9, 1993

[86] PCT No.: PCT/EP93/00029

§ 371 Date: Oct. 18, 1993

§ 102(e) Date: Oct. 18, 1993

[87] PCT Pub. No.: WO93/16678

PCT Pub. Date: Sep. 2, 1993

[30] Foreign Application Priority Data

Feb. 28, 1992 [DE] Germany .......................... 42 06 236.5

[51] Int. Cl.⁶ ................................................. A61K 7/40
[52] U.S. Cl. ........................... 424/401; 8/405; 424/70.1; 424/70.11; 424/70.19
[58] Field of Search ................... 424/401, 70, 71, 424/70.1, 70.11, 70.19; 8/405

[56] References Cited

U.S. PATENT DOCUMENTS

| | | | |
|---|---|---|---|
| 2,449,070 | 9/1948 | Hauser | 424/61 |
| 3,193,465 | 7/1965 | Frowde | 8/405 |
| 4,402,698 | 9/1983 | Kalopissis et al. | 8/405 |
| 4,592,908 | 6/1986 | Wajaroff et al. | 424/71 |
| 4,938,954 | 7/1990 | Gross et al. | 424/71 |
| 5,000,938 | 3/1991 | De Boeck et al. | 424/47 |

FOREIGN PATENT DOCUMENTS

| | | |
|---|---|---|
| 0301197 | 1/1989 | European Pat. Off. . |
| 1322480 | 2/1963 | France . |
| 1571293 | 6/1969 | France . |

Primary Examiner—Melvyn I. Marquis
Assistant Examiner—Robert H. Harrison
Attorney, Agent, or Firm—Michael J. Striker

[57] ABSTRACT

The process of dyeing hair includes uniformly applying to a strip of skin adjoining the hair line of the hair to be dyed a protective composition containing 27 to 50 percent by weight polyethylene glycol having an average molecular weight of 2,700 to 7,500; 7 to 14 percent by weight hydrogenated castor oil, ethoxylated with 40 to 60 moles of ethylene oxide; 28 to 42 percent by weight glycerin and/or ethyl hexanediol and/or polyethylene glycol having a molecular weight of 100 to 300; at least one standard cosmetic additive; and 0 to 18 percent by weight water; to protect the strip of the skin from coloring when dyeing or tinting hair; then treating the hair to be dyed with the hair dye; and after the treating of the hair with the hair dye, subsequently rinsing or rinsing and shampooing the hair.

2 Claims, No Drawings

METHOD OF PREVENTING COLORING OF SKIN ADJACENT THE HAIRLINE DURING DYEING OF HAIR

BACKGROUND OF THE INVENTION

The present invention relates to the use of a preparation for preventing the coloring of skin when dyeing the hair, novel skin protection compositions, and a process for dyeing hair with the use of these skin protection compositions or said preparation.

When dyeing hair, even when the hair dye composition is applied with utmost care, coloring of the skin cannot always be avoided. This coloring of the skin is particularly unsightly and annoying on the visible parts of the skin directly adjoining the hairline.

Numerous so-called color-spot removers are known which can be employed after the hair dyeing treatment is concluded for removing the spots of color. Regardless of the composition employed, subsequent removal of spots of color is always irritating to the skin due to the cleaning materials contained in the compositions and the mechanical rubbing which is generally required to remove the spots of color. In addition, these color-spot removers are often not capable of entirely eliminating the color from the skin once it has occurred.

Therefore, to prevent the coloring of skin when dyeing hair, skin creams in the form of oil-in-water emulsions or water-in-oil emulsions and petrolatum are applied directly to the skin adjoining the hairline before beginning the dyeing treatment.

However, it has been shown that the use of skin protection compositions in the form of emulsions, particularly in hair dyeing treatments with dark, color-intensive shades, does not adequately protect the skin from coloring and subsequent treatment with a color-spot remover is required.

Vaseline is unsuitable as protection against coloring of the skin when dyeing the hair, since its insolubility in water makes it very difficult to remove again from the skin adjoining the hairline without the use of organic solvents such as acetone or benzene.

Therefore, the problem is posed of providing a preparation of use in preventing the coloring of skin when dyeing or tinting hair which is easy to apply and safely protects the skin adjoining the hairline from being colored when dyeing or tinting the hair. It should be possible to remove this preparation easily and completely with water after the dyeing treatment or after tinting and the preparation should also be tolerated well by the skin.

SUMMARY OF THE INVENTION

Accordingly, it is an object of the present invention to provide a new process of dyeing hair as well as compositions to prevent skin coloring and to protect skin during dyeing with improved qualities.

Surprisingly, it has now been found that the problem specified above is solved in an outstanding manner by the use of a preparation which is characterized in that it contains a combination of (A) 27 to 50 percent by weight polyethylene glycol with an average molecular weight of 2700 to 7500, (B) 7 to 14 percent by weight hydrogenated castor oil ethoxylated with 40 to 60 moles ethylene oxide, (C) 28 to 42 percent by weight glycerin and/or ethyl hexanediol and/or polyethylene glycol with a molecular weight of 100 to 300, and (D) 0 to 18 percent by weight water to protect the skin from coloring when dyeing or tinting hair.

The subject matter of the present invention is also a skin protection composition which is characterized in that it contains a combination of (A) 25 to 40 percent by weight polyethylene glycol with an average molecular weight of 2700 to 4800, (B) 2 to 10 percent by weight polyethylene glycol with an average molecular weight of 5600 to 9000, (C) 7 to 14 percent by weight hydrogenated castor oil ethoxylated with 40 to 60 moles ethylene oxide, (D) 28 to 42 percent by weight glycerin and/or ethyl hexanediol and/or polyethylene glycol with a molecular weight of 100 to 300, and (E) 0 to 18 percent by weight water.

Due to its highly viscous, waxy, glue-like consistency, the skin protection composition according to the invention ensures an excellent protection against coloring of the skin when dyeing the hair, particularly also when dyeing the hair in dark shades. The skin protection composition can be effortlessly applied in a uniform manner prior to the hair dyeing treatment, is very well tolerated by the skin, and can be removed again easily and completely with water after the hair dyeing treatment.

In a particularly preferred embodiment form, the skin protection composition according to the invention contains (A) 28 to 32 percent by weight polyethylene glycol with an average molecular weight of 2700 to 4800, (B) 2 to 7 percent by weight polyethylene glycol with an average molecular weight of 5600 to 9000, (C) 8 to 13 percent by weight hydrogenated castor oil ethoxylated with 40 to 60 moles ethylene oxide, (D) 33 to 38 percent by weight glycerin and/or ethyl hexanediol and/or polyethylene glycol with a molecular weight of 100 to 300, and (E) 5 to 14 percent by weight water.

In addition to the components (A) to (E) mentioned above, the preparation as well as the skin protection composition according to the invention can also contain conventional and known additives for cosmetic compositions such as perfume oils in quantities of 0.1 to 2 percent by weight; preservatives, e.g. benzoic acid, mandelic acid, salicylic acid, sorbic acid, formaldehyde, p-hydroxybenzoic acid ester, mixtures of methyl chloroisothiazolinon and methyl isothiazolinon or 5-chloro-2-(2,4-dichlorophenoxy)phenol in quantities of 0.1 to 1 percent by weight; skin-care materials such as allantoin, α-bisabolol, glycyrrhetinic acid, myristyl lactate or cetyl lactate in quantities of 0.1 to 2 percent by weight; consistency regulators such as montmorillonite or alkali montmorillonite in quantities of 0.1 to 8 percent by weight, as well as film formers such as chitosan lactate in quantities of 0.1 to 1 percent by weight.

The present invention is further directed to a process for dyeing hair in which a sufficient quantity, generally 5 to 10 grams, of the preparation mentioned above or of a skin protection composition according to the invention is uniformly applied to the skin adjoining the hairline, normally in a width of 1 to 2 cm, possibly with the use of a spatula, and the hair is then treated with hair dye. The dyed hair is then rinsed with water, possibly washed with a shampoo, and treated with a hair-care composition which can be rinsed out with water.

The preparation or skin protection composition according to the invention which was applied beforehand is removed simultaneously during the washing and rinsing.

DESCRIPTION OF PREFERRED EMBODIMENTS

Hereinbelow several examples are presented to show preferred embodiments of the process as well as compositions in accordance with the present invention in greater detail, in form of examples.

EXAMPLE 1

Skin Protection Composition

| | |
|---|---|
| 30.00 g | polyethylene glycol with an average molecular weight of 2700 to 4800 |
| 5.00 g | polyethylene glycol with an average molecular weight of 5600 to 9000 |
| 10.00 g | hydrogenated castor oil, ethoxylated with 40 to 60 moles ethylene oxide |
| 35.26 g | glycerin |
| 4.65 g | sodium montmorillonite |
| 1.00 g | myristyl lactate |
| 0.01 g | chitosan lactate |
| 0.20 g | p-hydroxybenzoic acid methyl ester |
| 0.10 g | salicylic acid |
| 0.30 g | perfume oil |
| 13.48 g | water |
| 100.00 g | |

EXAMPLE 2

Skin Protection Composition

| | |
|---|---|
| 30.00 g | polyethylene glycol with an average molecular weight of 2700 to 4800 |
| 5.00 g | polyethylene glycol with an average molecular weight of 5600 to 9000 |
| 10.00 g | hydrogenated castor oil, ethoxylated with 40 to 60 moles ethylene oxide |
| 35.26 g | glycerin |
| 4.65 g | sodium montmorillonite |
| 1.00 g | myristyl lactate |
| 0.01 g | chitosan lactate |
| 0.20 g | p-hydroxybenzoic acid methyl ester |
| 0.10 g | sorbic acid |
| 0.50 g | α-bisabolol |
| 0.30 g | perfume oil |
| 10.58 g | water |
| 100.00 g | |

EXAMPLE 3

Skin Protection Composition

| | |
|---|---|
| 30.00 g | polyethylene glycol with an average molecular weight of 2700 to 4800 |
| 5.00 g | polyethylene glycol with an average molecular weight of 5600 to 9000 |
| 10.00 g | hydrogenated castor oil, ethoxylated with 40 to 60 moles ethylene oxide |
| 35.26 g | ethyl hexanediol |
| 4.65 g | sodium montmorillonite |
| 1.00 g | myristyl lactate |
| 0.01 g | chitosan lactate |
| 0.20 g | p-hydroxybenzoic acid methyl ester |
| 0.10 g | salicylic acid |
| 0.30 g | perfume oil |
| 13.48 g | water |
| 100.00 g | |

EXAMPLE 4

Skin Protection Composition

| | |
|---|---|
| 30.00 g | polyethylene glycol with an average molecular weight of 2700 to 4800 |
| 5.00 g | polyethylene glycol with an average molecular weight of 5600 to 9000 |
| 12.40 g | hydrogenated castor oil, ethoxylated with 40 to 60 moles ethylene oxide |
| 35.26 g | polyethylene glycol with a molecular weight of 100 to 300 |
| 4.65 g | sodium montmorillonite |
| 1.00 g | myristyl lactate |
| 0.01 g | chitosan lactate |
| 0.20 g | p-hydroxybenzoic acid methyl ester |
| 0.10 g | sorbic acid |
| 0.50 g | α-bisabolol |
| 0.30 g | perfume oil |
| 10.58 g | water |
| 100.00 g | |

The skin protection composition according to Examples 1 to 4 is produced by melting and mixing together the components at 650° C. The homogenous melt of the skin protection composition is then cooled accompanied by stirring and placed in a crucible at 45° to 55° C.

EXAMPLE 5

Process for Dyeing Hair

Blond natural hair is first moistened with water. 7.5 grams of the skin protection composition, according to the invention, from Example 4 are then uniformly applied to the skin in a width of 1 to 2 cm adjoining the hairline. Then 50 g of a hair dye of the following composition

| | |
|---|---|
| 1.00 g | 4-amino-2[bis-(2'-hydroxyethyl)aminomethyl]phenol |
| 1.10 g | 1-naphthol |
| 15.00 g | cetyl alcohol |
| 0.30 g | sodium sulfite, anhydrous |
| 3.50 g | lauryl alcohol diglycol ether sulfate sodium salt (28-percent aqueous solution) |
| 3.00 g | ammonia (22-percent aqueous solution) |
| 76.10 g | water |
| 100.00 g | | are mixed with 50 g hydrogen peroxide solution (6 percent) shortly before use. The mixture is then applied to the blond natural hair and allowed to act for 30 minutes at 40° C.

The hair is then rinsed with water and the skin protection composition is removed simultaneously. The hair is then dried. The hair is dyed an intensive red color. The skin adjoining the hairline has been effectively protected against coloring by the skin protection composition.

All of the percentages indicated in the present application are percent by weight.

While the invention has been illustrated and described as embodied in a method of preventing coloring of skin adjacent the hairline during dyeing of hair, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

1. A process of dyeing hair, consisting of the steps of:

a) uniformly applying to a strip of skin adjoining a hairline of the hair to be dyed a protective composition consisting essentially of 27 to 50 percent by weight polyethylene glycol having an average molecular weight of 2,700 to 7,500; 7 to 14 percent by weight hydrogenated castor oil, said hydrogenated caster oil being ethoxylated with 40 to 60 moles of ethylene oxide; 28 to 42 percent by weight of at least one member selected from the group consisting of glycerin, ethyl hexanediol and polyethylene glycol having a molecular weight of 100 to 300; and 0 to 18 percent by weight water to protect the strip of said skin from coloring when dyeing or tinting hair;

b) then treating the hair to be dyed with a hair dye to dye the hair; and c) after the treating of the hair with the hair dye, subsequently rinsing or rinsing and shampooing the hair such that said protective composition is simultaneously removed during said rinsing or said rinsing and shampooing the hair.

2. A process of dyeing hair, consisting of the steps of:

a) uniformly applying to a strip of skin adjoining a hairline of the hair to be dyed a protective composition consisting of 28 to 32 percent by weight polyethylene glycol having an average molecular weight of 2,700 to 4,800; 2 to 7 percent by weight polyethylene glycol having an average molecular weight of 5,600 to 9,000; 8 to 13 percent by weight hydrogenated castor oil, said hydrogenated caster oil being ethoxylated with 40 to 60 moles of ethylene oxide; 33 to 38 percent by weight of at least one member selected from the group consisting of glycerin, ethyl hexanediol and polyethylene glycol having a molecular weight of 100 to 300; 0.1 to 1 percent by weight chitosan lactate; 0.1 to 8 percent by weight of an alkali metal montmorillonite; 0.1 to 2 percent by weight of at least one skin-care member selected from the group consisting of allantoin, α-bisabolol, glycyrrhetinic acid, myristyl lactate and cetyl lactate; 0.1 to 1 percent by weight of at least one preservative compound selected from the group consisting of benzoic acid, mandelic acid, salicylic acid, sorbic acid, formaldehyde, p-hydroxybenzoic acid ester, 5-chloro-2-(2,4-dichlorophenoxy)phenol and mixtures of methyl chloroisothiazolinon and methyl isothiazolinon, 0.1 to 2 percent by weight perfume oil and 5 to 14 percent by weight water to protect said strip of said skin from being dyed when dyeing or tinting hair;

b) then treating the hair to be dyed with a hair dye to dye the hair; and c) after the treating of the hair with the hair dye, subsequently rinsing or rinsing and shampooing the hair such that said protective composition is simultaneously removed during said rinsing or said rinsing and shampooing the hair.

* * * * *